US008213565B2

(12) United States Patent
Boese et al.

(10) Patent No.: US 8,213,565 B2
(45) Date of Patent: Jul. 3, 2012

(54) METHOD FOR CORRECTING TRUNCATED PROJECTION DATA

(75) Inventors: Jan Boese, Eckental (DE); Klaus Klingenbeck, Wüstenstein/Wiesenttal (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 12/891,849

(22) Filed: Sep. 28, 2010

(65) Prior Publication Data

US 2011/0075798 A1   Mar. 31, 2011

(30) Foreign Application Priority Data

Sep. 30, 2009  (DE) .......................... 10 2009 047 867

(51) Int. Cl.
*A61B 6/00*   (2006.01)
(52) U.S. Cl. .............................. 378/4; 378/20
(58) Field of Classification Search ................. 378/4, 20
See application file for complete search history.

(56) References Cited

U.S. PATENT DOCUMENTS

| | | | | |
|---|---|---|---|---|
| 4,550,371 A * | 10/1985 | Glover et al. ..................... 378/4 |
| 4,920,491 A * | 4/1990 | Eberhard et al. ............... 382/131 |
| 5,032,990 A * | 7/1991 | Eberhard et al. .................. 378/4 |
| 5,053,958 A * | 10/1991 | Tam ................................. 378/4 |
| 5,319,693 A * | 6/1994 | Eberhard et al. ................ 378/19 |
| 5,740,224 A * | 4/1998 | Muller et al. .................... 378/11 |
| 5,838,765 A * | 11/1998 | Gershman et al. ............ 378/196 |
| 6,246,742 B1 * | 6/2001 | Besson et al. ..................... 378/8 |
| 6,459,094 B1 * | 10/2002 | Wang et al. .................... 250/584 |
| 6,546,068 B1 * | 4/2003 | Shimura ......................... 378/19 |
| 6,810,102 B2 * | 10/2004 | Hsieh et al. ....................... 378/4 |
| 6,915,005 B1 * | 7/2005 | Ruchala et al. ............... 382/131 |
| 7,362,843 B2 * | 4/2008 | Basu et al. ........................ 378/4 |
| 7,372,935 B2 * | 5/2008 | Bernhardt et al. ................ 378/4 |
| 7,440,535 B2 * | 10/2008 | Netsch et al. .................... 378/4 |
| 7,500,784 B2 | 3/2009 | Grebner et al. |
| 7,570,733 B2 * | 8/2009 | Hsieh et al. ....................... 378/8 |
| 7,630,473 B2 * | 12/2009 | Scholz ............................ 378/18 |
| 2006/0062443 A1 * | 3/2006 | Basu et al. .................... 382/131 |
| 2006/0120507 A1 | 6/2006 | Brunner et al. |

FOREIGN PATENT DOCUMENTS

| | | |
|---|---|---|
| DE | 102005022540 B4 | 7/2007 |
| DE | 102006061178 A1 | 6/2008 |
| DE | 102008003945 B3 | 7/2009 |

OTHER PUBLICATIONS

Patrick Kurp, AXIOM Artis FD Systems DynaCT—"A Breakthrough in Interventional 3D Imaging" Reprint from Medical Solutions, Jan. 2005, pp. 46-51.
Ohnesorge et al., "Efficient correction for CT image artifacts caused by objects extending outside the scan field of view", Med. Phys. 27, 2000, pp. 39-46, vol. 1.
Feldkamp et al., Journal of the Optical Society of America, Jun. 1984, pp. 612-619, vol. 1, No. 6.

* cited by examiner

*Primary Examiner* — Alexander H Taningco

(57) ABSTRACT

A method for correcting truncated projection data of a rotation for a reconstruction technique for computed tomography scans with truncated projection data in the computed tomography images produced by a C-arm is proposed. At least one truncated projection is recorded. The truncated portions prior to acquisition of the rotation for the at least one truncated projection is captured. The truncated projection and the truncated portions are assembled into at least one complete projection. Truncated projection data is acquired during the rotation. The truncated data is estimated based on a model of the patient geometry from the at least one complete projection. A reconstruction technique is performed on the basis of the acquired and the estimated data.

11 Claims, 4 Drawing Sheets

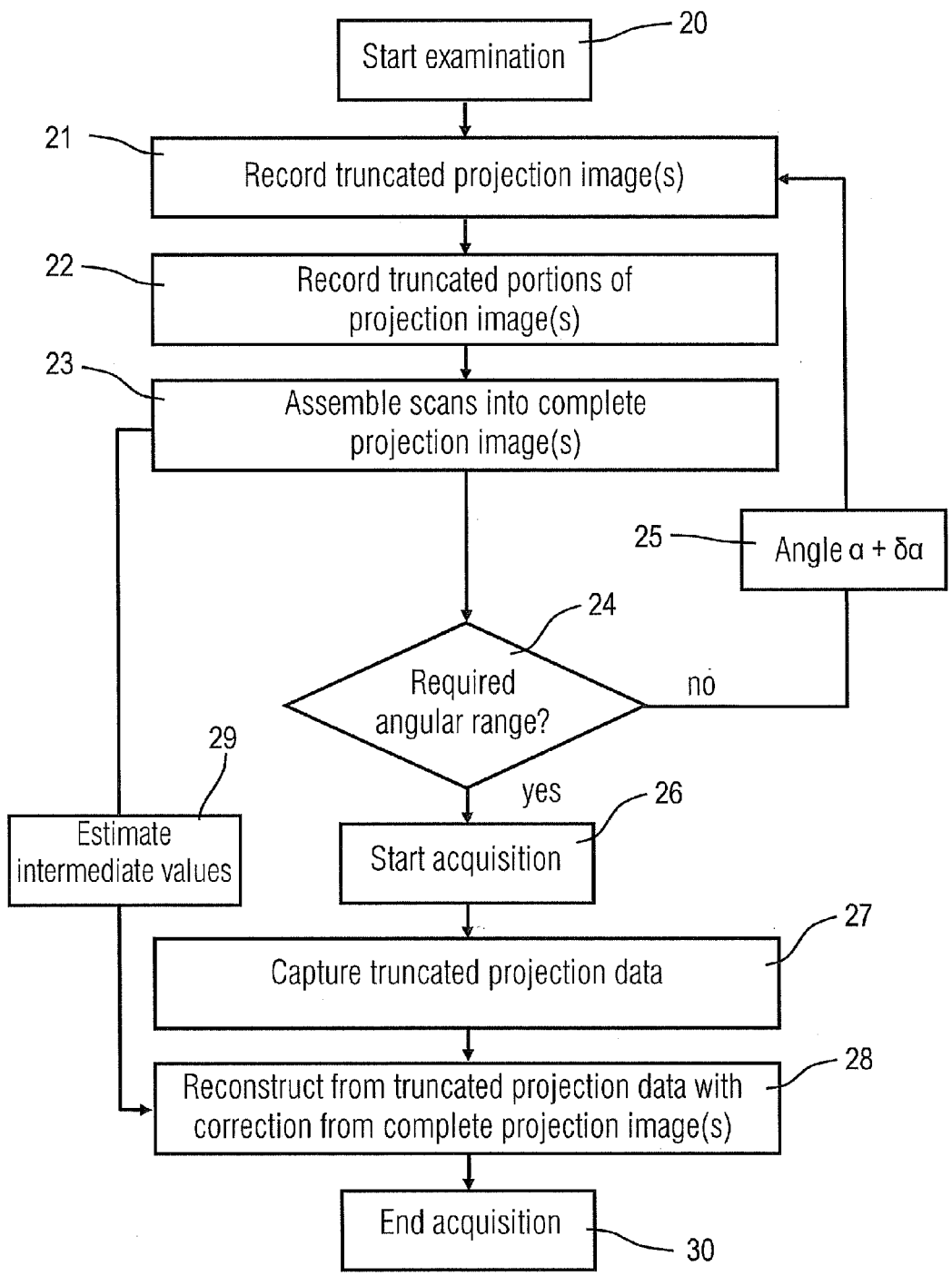

METHOD FOR CORRECTING TRUNCATED PROJECTION DATA

CROSS REFERENCE TO RELATED APPLICATIONS

This application claims priority of German application No. 10 2009 047 867.1 filed Sep. 30, 2009, which is incorporated by reference herein in its entirety.

FIELD OF THE INVENTION

The invention relates to a method for correcting truncated projection data of a rotation for a reconstruction technique for computed tomography scans with truncated projection data in the computed tomography images obtained using a C-arm.

BACKGROUND OF THE INVENTION

The integration of digital flat panel detectors into the C-arm of angiography systems allows CT-like imaging in the angiography laboratory. In the case of these C-arm computed tomography scans it may happen that the object to be imaged extends beyond the scan field of view, with the result that data capture produces truncated projection data.

CT-like imaging means in particular generating volume images with low-contrast resolution which allows different soft tissues to be differentiated. An example of this is the product DynaCT of Siemens AG, Medical Solutions, based on the AXIOM Artis systems as described, for example, in AXIOM Artis FD Systems—DynaCT—A Breakthrough in Interventional 3D Imaging, by Patrick Kurp, Reprint from Medical Solutions, January 2005, pages 46 to 51, or as disclosed in US 2006/0120507 A1.

FIG. 1 shows an x-ray diagnostic device which has a C-arm 2 rotatably mounted on a stand in the form of a 6-axis industrial robot or articulated arm robot 1, at the ends of which C-arm are mounted an x-ray source, e.g. an x-ray emitter 3, and an x-ray detector 4 as an image capture unit. The above-mentioned CT-like imaging can be performed using x-ray diagnostic equipment of this kind, for example.

By means of the articulated arm robot 1 disclosed in U.S. Pat. No. 7,500,784 B2, for example, which preferably has six axes of rotation and therefore six degree of freedom, the C-arm 2 can be placed in any spatial position by rotating it, for example, about a rotation center between the x-ray emitter 3 and the x-ray detector 4. The inventive x-ray system 1 to 4 is in particular rotatable about centers of rotation and axes of rotation in the C-arm plane of the x-ray detector 4, preferably about the center of the x-ray detector 4 and about axes of rotation intersecting the center of the x-ray detector 4.

The known articulated arm robot 1 has a base frame which is e.g. fixed to a base. Rotatably mounted thereon about a first axis of rotation is a carousel. Pivotally mounted on the carousel about a second axis of rotation is a rocker arm on which a robotic arm is rotatably mounted about a third axis of rotation. Rotatably mounted to the end of the robot arm about a fourth axis of rotation is a robotic hand. The robotic hand has a fixing element for the C-arm 2 which is pivotable about a fifth axis of rotation and rotatable about a sixth axis of rotation running perpendicular thereto.

The implementation of the x-ray diagnostic device is not dependent on the industrial robot. Normal C-arm machines can also be used.

The x-ray detector 4 can be a rectangular or square flat semiconductor detector made of amorphous silicon (a-Si), referred to as a digital flat panel detector.

Located in the beam path of the x-ray emitter 3 is a laterally displaceable and height-adjustable patient positioning table 5 for use in angiography for scanning e.g. the heart of a patient 6 to be examined as an examination subject. A system control unit 7 comprising an imaging system 8 which receives and processes the image signals of the x-ray detector 4 is connected to the x-ray diagnostic device. The x-ray images can then be viewed on a monitor 9.

The x-ray emitter 3 emits a radiation beam 10 originating from a beam focus of its x-ray source which is incident on the x-ray detector 4. If 3D datasets are to be produced in accordance with the above mentioned DynaCT method, the rotatably mounted C-arm 2 with x-ray emitter 3 and x-ray detector 4 is rotated such that, as shown schematically in FIG. 2 in plan view onto the axis of rotation, the x-ray emitter 3 here represented pictorially by its beam focus and the x-ray detector 4 move in an orbit 12 around an examination subject 11 located in the beam path of the radiation beam 10 of the x-ray emitter 3. The orbit 12 can be completely or partially traveled to produce a 3D dataset.

Data acquisition takes place during rotation of the C-arm around the examination subject 11, the focus of the x-ray emitter 3 moving on a predefined trajectory, e.g. on a graduated circle, the oppositely disposed x-ray detector 4 recording two-dimensional projection images. The latter are used as two-dimensional projections from which the volume dataset is computed using known cone beam CT algorithms such as the so-called Feldkamp algorithm, as described by Feldkamp et al. in the article "Practical cone-beam algorithm", Journal of the Optical Society of America, Vol. 1, No. 6, Jun. 1984, pages 612 to 619.

According to the DynaCT method, the C-arm 2 with x-ray emitter 3 and x-ray detector 4 preferably moves through an angular range of at least 180°, e.g. 180° plus fan angle, and captures projection images from different projections in rapid succession. Reconstruction may only take place from a portion of this captured data.

The examination subject 11 can be, for example, an animal or human body or even a phantom.

The x-ray emitter 3 and the x-ray detector 4 each move around the subject 11 such that the x-ray emitter 3 and the x-ray detector 4 are on diametrically opposite sides of the subject 11.

In normal radiography or fluoroscopy by means of an x-ray diagnostic device of this kind, the 2D medical data of the x-ray detector 4 may be buffered in the imaging system 8 and subsequently displayed on the monitor 9.

As the digital flat panel detectors currently used as x-ray detectors 4 have limited field sizes, e.g. $30 \times 40 \text{ cm}^2$ in the case of AXIOM Artis, for larger organ areas such as in the thorax and abdomen it is not possible to map the anatomy in question completely onto the x-ray detector 4. This means that the two-dimensional projection is unable to capture edges of the organ area.

However, with cut-off, i.e. truncated, projections of said kind, artifacts are produced in the volume images in the reconstruction, said artifacts in some cases masking details of the anatomy captured. For more accurate reconstruction, therefore, a truncation correction is applied to the projections. To achieve this, various methods are known from the relevant literature which basically consist of extrapolating the truncated projections at the edge to zero on the basis of a model, see e.g. Bernd Ohnesorge et al., "Efficient correction for CT image artifacts caused by objects extending outside the scan field of view", Med Phys, Vol. 1, pages 39 to 46, 2000.

SUMMARY OF THE INVENTION

The object of the invention is to approximate this extrapolation as closely as possible to the actual conditions of the untruncated projection by supplementing the projection data with a priori information.

This object is achieved according to the invention by the features set forth in the independent claim. Advantageous embodiments are detailed in the dependent claims.

In an above-mentioned method this is achieved by the following steps:
i) recording at least one truncated projection,
ii) capturing the truncated portions prior to acquisition of the rotation for the at least one truncated projection,
iii) assembly into at least one complete projection,
iv) acquisition of truncated projection data during the rotation,
v) estimation of the truncated data based on a model of the patient geometry from the at least one complete projection, and
vi) performance of a reconstruction technique on the basis of the acquired and the estimated data.

This provides a priori information which can be used for correcting truncated projections in C-arm CT.

It has been found advantageous for the truncated portions according to step ii) to be captured by lateral and/or vertical displacement of the patient positioning table.

According to the invention, assembly into at least one complete projection according to step iii) can be performed using an image processing technique (image stitching).

Automation of the method could inventively comprise the following steps:
a) positioning the radiation source and x-ray detector at an angle α,
b) centering the patient positioning table,
c) recording a truncated projection image as a first partial image,
d) displacing the patient positioning table laterally and/or vertically so that truncations no longer occur at the right-hand edge of the x-ray detector,
e) recording a second partial image as in step c),
f) displacing the patient positioning table laterally and/or vertically so that truncations no longer occur at the left-hand edge of the x-ray detector,
g) recording a third partial image as in step c),
h) assembling the partial images obtained from steps c), e) and g) into a complete projection image of angle α,
i) positioning the radiation source and x-ray detector at a new angle α+δα increased by an increment δα, and
j) repeating steps b) to i) until the required angular range has been captured.

The partial images can advantageously be captured as single images or as a plurality of single images summated for noise reduction.

According to the invention, the increment δα=15°.

Instead of stepwise displacement, the patient positioning table according to steps d) and f) can be displaced continuously and a series of images obtained during the continuous displacement which are assembled in accordance with step h).

The object is also achieved according to the invention by a device for performing the method in a reconstruction technique for in the reconstructed computed tomography images
1) having a radiation source for emitting divergent radiation with which an examination subject on a patient positioning table is scanned in different projection directions,
2) having an x-ray detector for detecting the radiation that has passed through the examination subject,
3) having an imaging system for reconstructing the computed tomography scans with truncated projection data, and
4) having a processing unit for assembling images and estimating intermediate values.

According to the invention the processing unit can be embodied such that the assembling of scans according to feature 4) is performed on the basis of the "image stitching" image processing technique.

The processing unit can be advantageously embodied such that a plurality of single images are summated for noise reduction.

BRIEF DESCRIPTION OF THE DRAWINGS

The invention will now be explained in greater detail with reference to exemplary embodiments illustrated in the accompanying drawings, in which:

FIG. 6 shows a flow chart of the normal course of the method according to the invention.

DETAILED DESCRIPTION OF THE INVENTION

Figure 1:
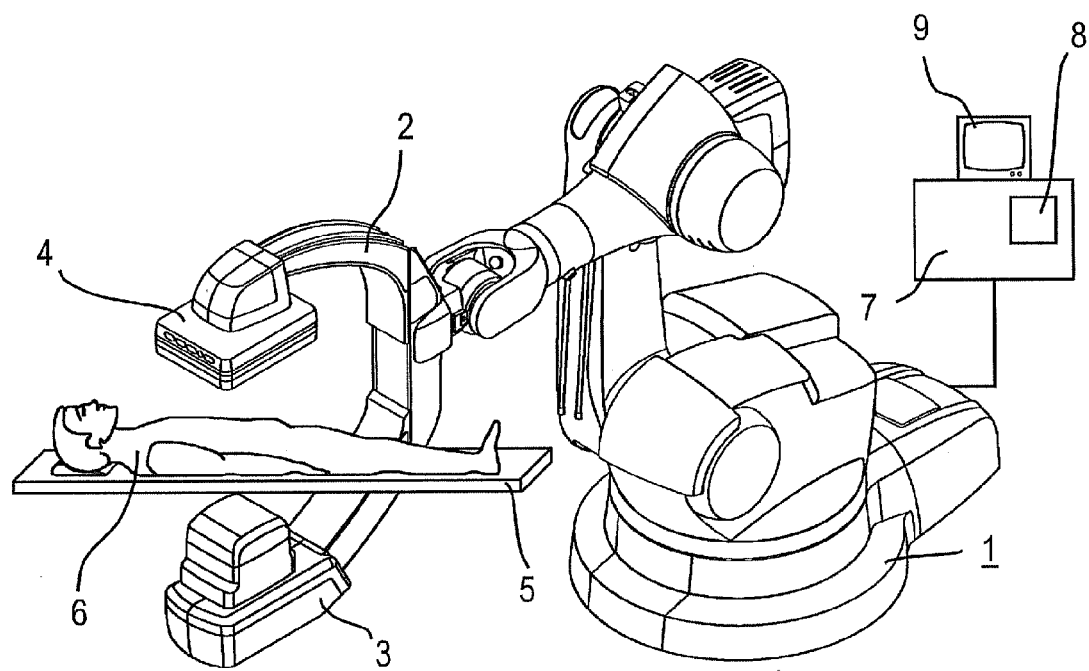
FIG. 1 shows a known C-arm x-ray system with an industrial robot as a supporting device.
Figure 2:
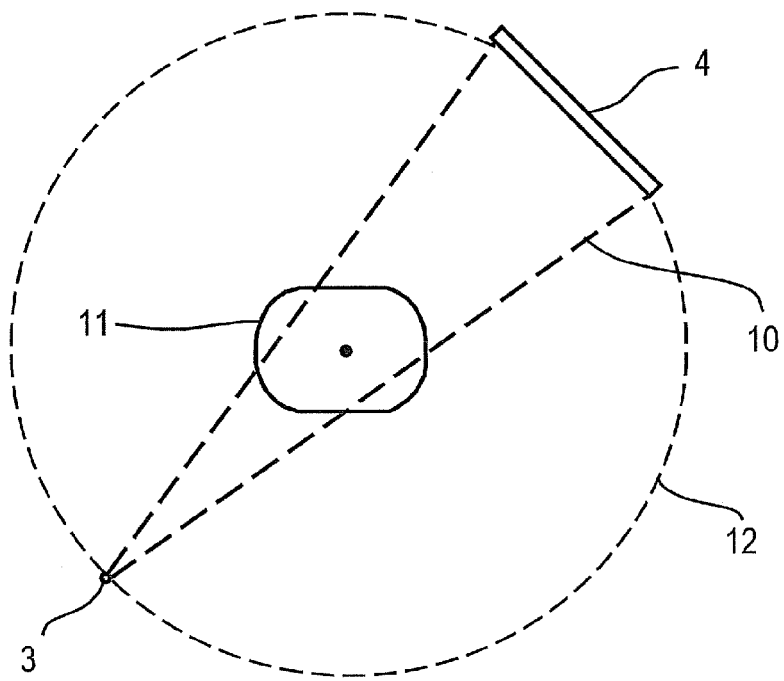
FIG. 2 shows a view of the path of an x-ray detector and of a radiation source according to FIG. 1 around an examination subject viewed in the axial direction.
Figure 3:
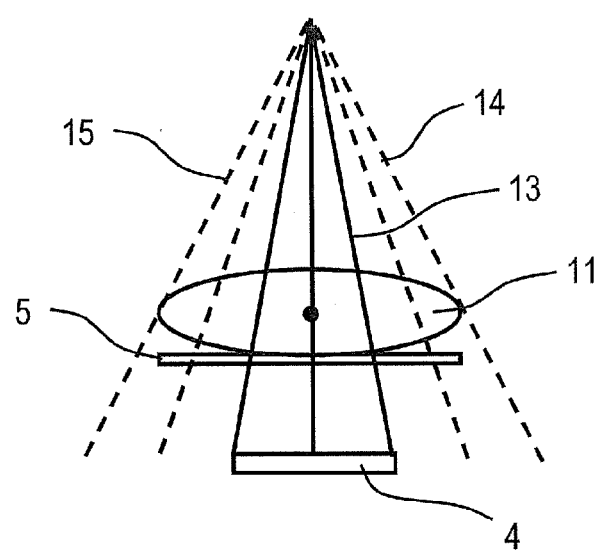
FIG. 3 shows a truncated cone beam projection according to the prior art.

The method according to the invention will now be explained in greater detail with reference to FIGS. 3 to 5. FIG. 3 shows a truncated cone beam projection according to the prior art in which only first rays 13 of the radiation beam 10 pass through the examination subject 11 and are incident on the x-ray detector 4, thereby producing a first partial image which corresponds to a normal truncated projection image. Second rays 14 and third rays 15 are not incident on the x-ray detector 4, with the result that the known cone beam projection detected by the x-ray detector 4 is truncated. Said radiation beam 10 originating from the beam focus of the x-ray emitter is laterally delimited such that the second and third rays 14 and 15 do not pass through the patient. These rays are used merely to facilitate understanding of the following figures and are therefore also shown only as dashed lines.

Figure 4:
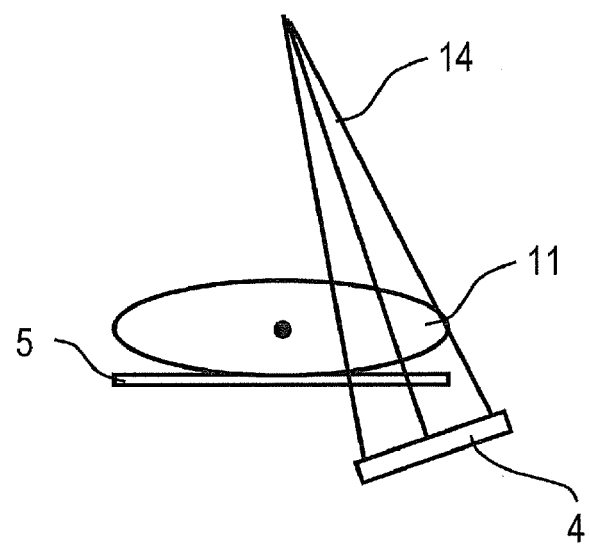
FIG. 4 shows a first cone beam projection.
Figure 5:
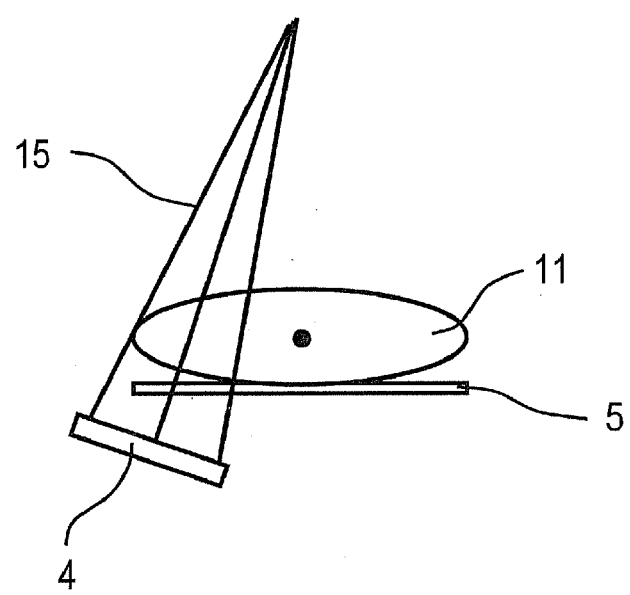
FIG. 5 shows a second cone beam projection according to the inventive method for completing the truncated cone beam projection.

FIG. 4 sketches in outline how a second projection image of the cut-off portion is produced. For this purpose the detector 4, the x-ray emitter 3 and/or the patient positioning table 5 are displaced such that the conditions as shown in FIG. 4 obtain. On the basis of this scanning geometry, the second rays 14 are detected by the x-ray detector 4, thereby producing a second partial image. FIG. 5 shows how the third rays 15 penetrate the examination subject 11 in the left-hand truncated region and are incident on the x-ray detector 4 so that a third partial image is produced.

Since the three partial images—recorded with patient positioning table 5 centered 5 and displaced laterally left or right and/or upward—will overlap, image processing techniques (image stitching) can be used by the imaging system 8 to assemble the partial images into a complete two-dimensional projection image.

This complete projection image is used as a priori information for correcting truncated projections in C-arm CT.

Depending on the degree of accuracy, this procedure can be repeated for different projection angles, e.g. with an angular distance of δα=15°. If, during the actual rotation, truncated projections are captured at smaller angular increments, intermediate values can be interpolated to complete the truncated projections.

FIG. 6 now charts the normal course of the method according to the invention. With the start of the examination 20, recording 21 of one or more truncated projection images is performed. Recording 22 of the truncated portions of projection images is then initiated. In another step 23, the scans produced from steps 21 and 22 are assembled into untruncated projection images. In the subsequent interrogation 24 it is established whether the required angular range has been reached. If this is not the case, in step 25 the angle α is increased by an increment δα such that steps 21 to 24 can be carried out with the new angle α+δα. The increment δα can be e.g. 15°.

If the required angular range has been reached according to the interrogation 24, acquisition 26 is initiated. For this purpose, capture 27 of truncated projection data is performed during a rotation. From said truncated projection data, reconstruction 28 is then carried out using a correction from the untruncated projections produced in step 23, estimations 29 of intermediate values possibly taking place.

The estimations of the truncated data are based on a model of the patient geometry produced from the at least one complete projection so that, after acquisition of the rotation (data capture), the truncated projection data for reconstruction is corrected by the extension of other projections.

These estimations 29 can be performed e.g. by known interpolation methods. When reconstruction 28 is complete, the end of acquisition 30 is reached. The thus reconstructed 3D images can then be viewed on the monitor 9 in the known manner.

In the simplest case this procedure can be used to complete an AP or LR projection of the patient 6 and to estimate the extension of other projections on the basis of a model of the patient geometry.

As a general rule, however, it will be more accurate and produce better image results if this method is applied from a plurality of projection angles.

For intermediate projection angles, a corresponding complete projection can then be generated by interpolation from adjacent, complete 2D projections.

This patent application is based on the idea that, in an angiography system in which the patient positioning table can also be laterally displaced and adjusted vertically, prior to acquisition of the projections the examination subject is scanned from a number of directions and the truncated portions of the projection images are measured and recorded by additional scanning with lateral and/or vertical table displacement. Since the images—recorded with table centered and laterally displaced left or right—will overlap, image processing techniques (image stitching) can be used to assemble the partial images into a complete two-dimensional projection image.

In the simplest case this procedure is used to complete an AP or LR projection of the patient and to estimate the extension of other projections on the basis of a model of the patient geometry.

As a general rule, however, it will be more accurate and produce better image results if this method is applied from a plurality of projection angles, e.g. every 15 degrees.

For intermediate viewing angles, a corresponding complete projection can then be generated by interpolation from adjacent, complete 2D projections.

Automation of the method by the system control unit could take the following form:
a) tube and x-ray detector are positioned at angle α,
b) table is centered,
c) projection image is taken, either a single image or a plurality thereof which are summated for noise reduction,
d) table is laterally and/or vertically displaced so that truncation no longer occurs at the right-hand edge of the x-ray detector,
e) as c)
f) table is laterally and/or vertically displaced so that truncation no longer occurs at the left-hand edge of the x-ray detector,
g) as c)
h) partial images from c), e), g) are assembled into a complete projection for angle α,
i) tube and x-ray detector are positioned at angle α+δα (e.g. δα=15 degrees), and
j) repeat b) to i) until the required angular range has been captured.

Normal acquisition during continuous rotation of the C-aim and with centered table is initiated. For angles which coincide with an angle previously moved to in a), the complete exact projection data from h) is used to complete the truncated projections. For rotation angles not moved to in a), interpolation from adjacent complete projections is used to complete the truncated projections.

Because of the cone beam geometry, it is only approximately possible to combine the partial images (step h). In an improved variant of the method, for a particular angle α, not only an individual image is recorded, but a series of images during continuous displacement of the table.

The actually truncated projections can then be reconstructed from this data by resorting of the cone beam projections. An example has already been described with reference to FIGS. 3 to 5. In a first projection, the rays 14 and 15 are not incident on the x-ray detector 4 and would result in truncations. In the second projection according to FIG. 4, the second rays 14 are inventively recorded at a different angle and after displacement of the table and are used to complete the first projections according to FIG. 3. Correspondingly, the third projection of the third rays 15 can be used to complete the first projection according to FIG. 3.

Full completion of all the projections according to this method would require a small angular increment δα. However, known inter- or extrapolations can be used to fill the gaps between complete projections, thereby also enabling larger angular increments or, in the extreme case, just a single complete projection to be used.

The invention claimed is:

1. A method for correcting truncated projection data in computed tomography images of a patient recorded by an imaging recording device, comprising:
    acquiring truncated projection data of a patient during rotation of an imaging recording device until an angular range of projection data has been captured by:
        (a) recording a truncated projection image having at least one truncated portion of the patient;
        (b) recording the at least one truncated portions of the patient for the truncated projection;
        (c) assembling the truncated projection image and the at least one truncated portions into a complete projection;

(d) incrementing an angle of rotation in the angular range;

estimating intermediate values of the truncated projection data based on a geometry model of the patient from the complete projection; and reconstructing the truncated projection data based on the acquired truncated projection data and the estimated intermediate values of the truncated projection data.

2. The method as claimed in claim 1, wherein the truncated portions are captured by displacing a patient positioning table of the imaging recording device laterally and/or vertically.

3. The method as claimed in claim 1, wherein the complete projection is assembled by image stitching.

4. The method as claimed in claim 1, further comprising:

positioning a radiation source and an x-ray detector of the imaging recording device at an angle $\alpha$;

centering a patient positioning table of the imaging recording device;

recording the truncated projection as a first partial image;

displacing the patient positioning table laterally and/or vertically so that truncation no longer occurs at a right-hand edge of the x-ray detector;

recording a second partial image;

displacing the patient positioning table laterally and/or vertically so that truncations no longer occur at a left-hand edge of the x-ray detector;

recording a third partial image;

assembling the first, the second, and the third partial images into a complete projection image of angle $\alpha$;

positioning the radiation source and the x-ray detector at a new angle $\alpha+\delta\alpha$ increased by an increment $\delta\alpha$; and repeating recording the first, the second and the third partial images until a required angular range has been captured.

5. The method as claimed in claim 4, wherein single images are captured for the first, the second, and the third partial images.

6. The method as claimed in claim 4, wherein a plurality of single images are captured for first, the second, and the third partial images and are summated for noise reduction.

7. The method as claimed in claim 4, wherein the increment $\delta\alpha=15°$.

8. The method as claimed in claim 4, wherein the patient positioning table is displaced continuously and a series of images are recorded for the second and the third partial images during the continuous displacement.

9. An imaging recording device, comprising:

a patient positioning for supporting a patient;

a radiation source for emitting divergent radiation for scanning an examination subject on the patient in different projection directions;

an x-ray detector for detecting the radiation that has passed through the examination subject for acquiring truncated projection data of a patient during rotation of an imaging recording device until an angular range of projection data has been captured by:

a) recording a truncated projection image having at least one truncated portion of the patient;

(b) recording the at least one truncated portions of the patient for the truncated projection image; and (c) incrementing an angle of rotation in the angular range;

a processing unit for:

assembling the truncated projection image and the at least one truncated portions into a complete projection; and estimating intermediate values of the truncated projection data based on a geometry model of the patient from the complete projection; and an imaging system for reconstructing the truncated projection data based on the acquired truncated projection data and the estimated intermediate values of the truncated projection data.

10. The device as claimed in claim 9, wherein the processing unit assembles the truncated projection image and the truncated portions into the complete projection by image stitching.

11. The device as claimed in claim 9, wherein a plurality of single images are captured for the truncated projection and the truncated portions and the processing unit summates the plurality of the single images for noise reduction.

* * * * *